United States Patent [19]

Pandey

[11] Patent Number: 5,210,226

[45] Date of Patent: May 11, 1993

[54] METHOD FOR SEPARATING AND PURIFYING POLYENE MACROLIDE ANTIBIOTICS

[75] Inventor: Ramesh C. Pandey, Libertyville, Ill.

[73] Assignee: Xechem Inc., New Brunswick, N.J.

[21] Appl. No.: 474,465

[22] Filed: Feb. 2, 1990

[51] Int. Cl.$^5$ ............................................. C07D 313/00
[52] U.S. Cl. ..................................... 549/271; 210/656
[58] Field of Search ........................... 514/450; 549/271

[56] References Cited

U.S. PATENT DOCUMENTS 4,707,470 11/1987 Kirsh et al. ........................... 514/938
4,831,018 5/1989 Kirsh et al. ........................... 514/938

FOREIGN PATENT DOCUMENTS 0350430 1/1990 European Pat. Off. ............. 549/271

OTHER PUBLICATIONS

Wasserman et al "Biosynthesis of the mycoticins, metabolites of Streptomyces Ruber." CA 75 31631j (1971).
Merck Index #2880 (1983).

*Primary Examiner*—Alan L. Rotman
*Assistant Examiner*—A. A. Owens
*Attorney, Agent, or Firm*—W. Dennis Drehkoff

[57] ABSTRACT

The present invention provides for the first time an expeditious method to separate polyene macrolide antibiotics into their major components, through a general preparatory procedure employing high pressure liquid chromatography. The procedure allows for the first time a useable preparatory method for separating the polyene macrolide complexes derived from fermentation and cultivation of various organisms, into their major components. Substantially pure dermostatic A and dermostatic B can now be achieved as well as substantially pure mycoticin A and mycoticin B.

2 Claims, 26 Drawing Sheets

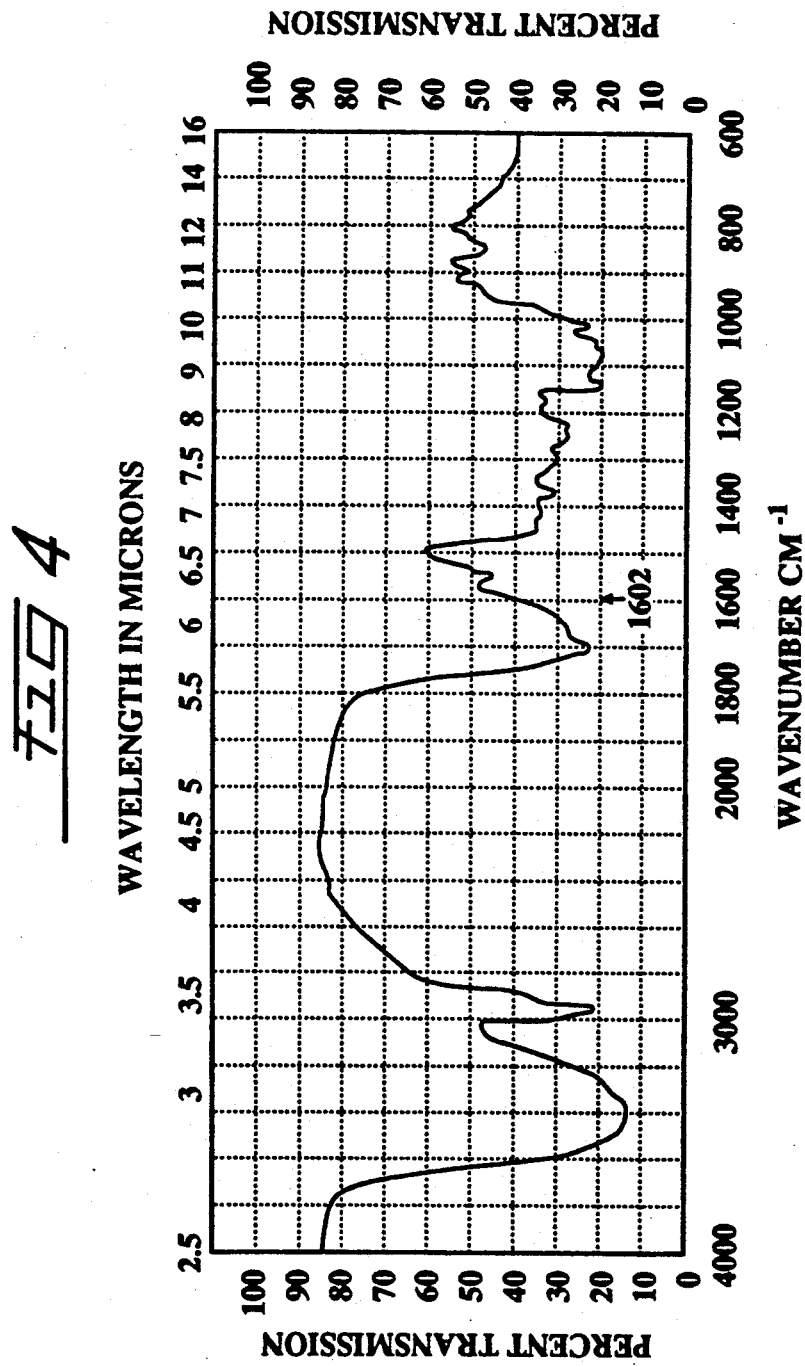

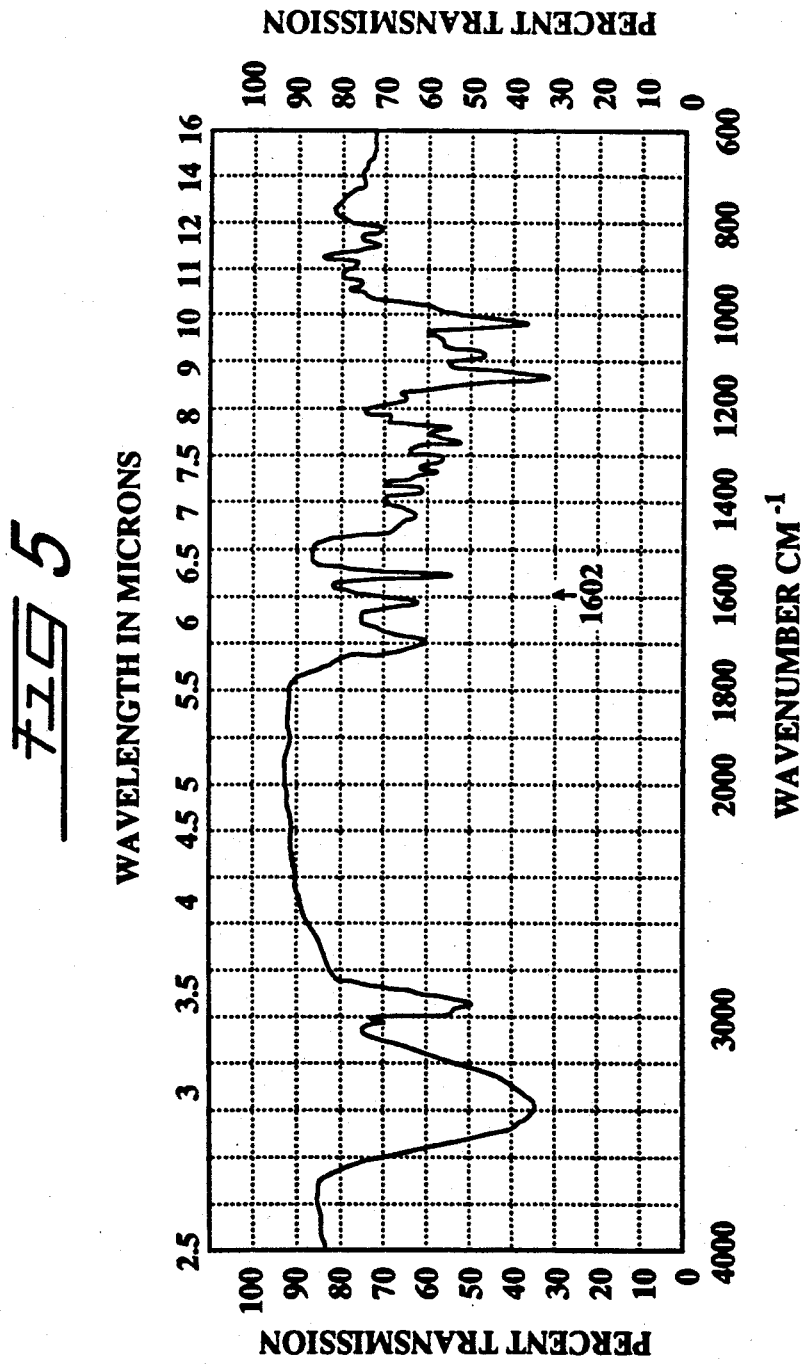

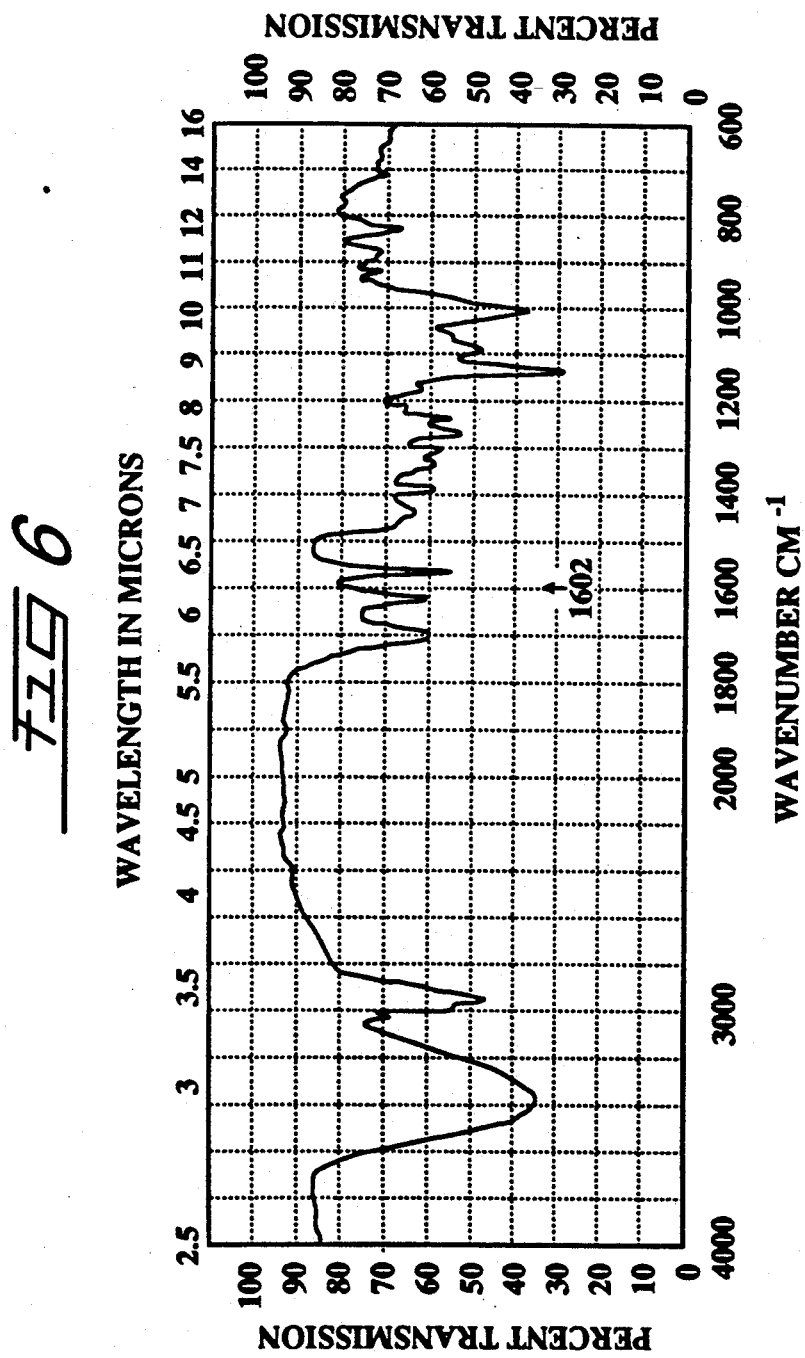

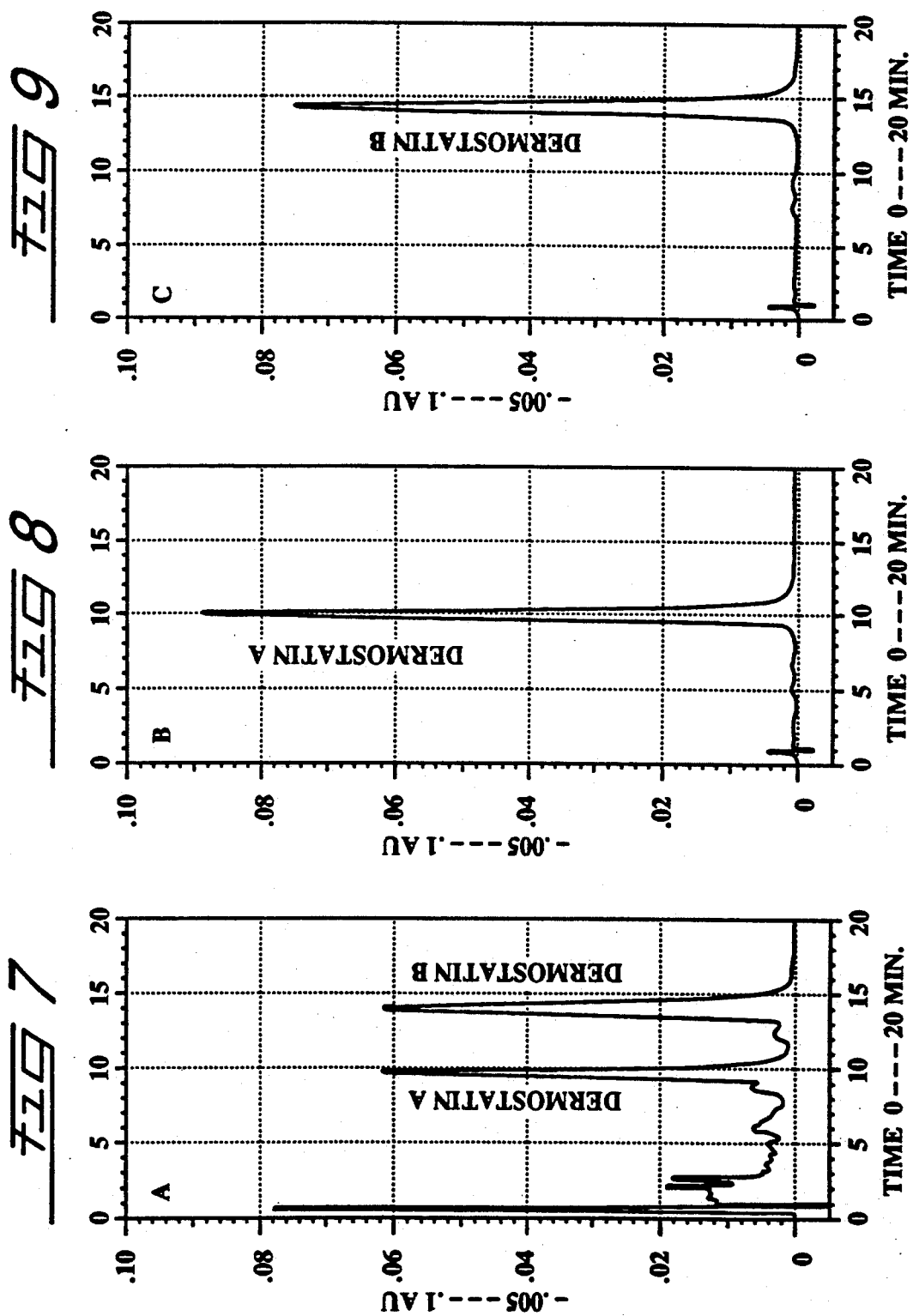

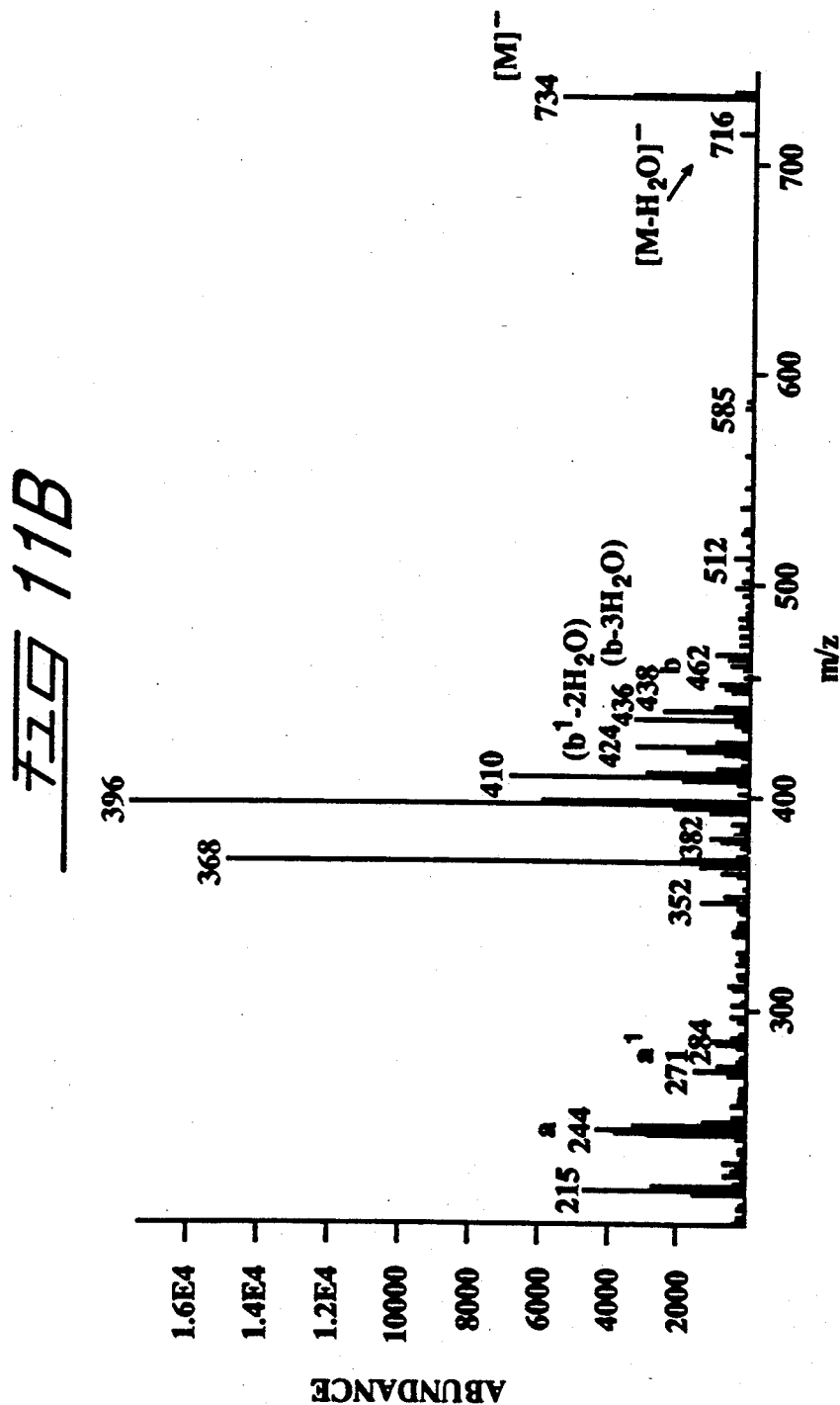

Dermostatin A

Dermostatin B

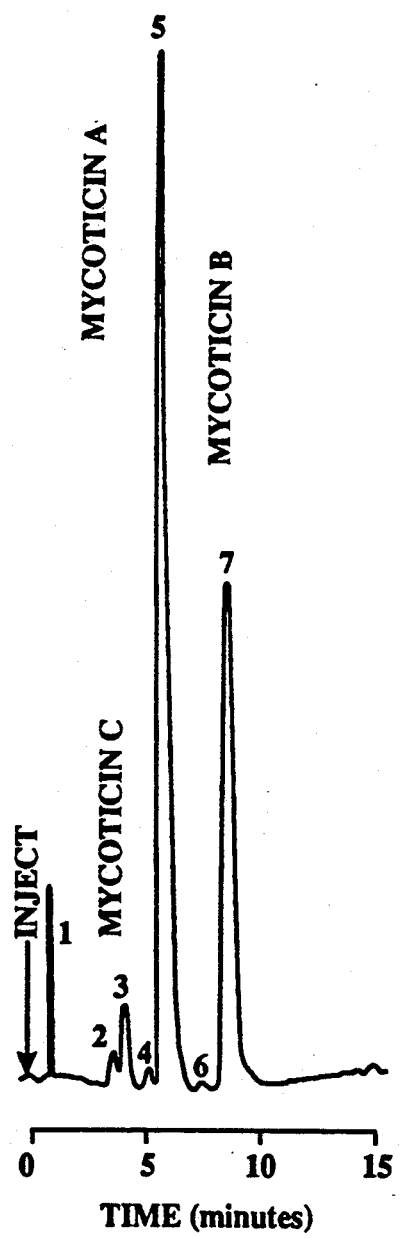

5,210,226

METHOD FOR SEPARATING AND PURIFYING POLYENE MACROLIDE ANTIBIOTICS

FIELD OF THE INVENTION

This invention relates generally to the field of pharmacology and more specifically to a method for separating and purifying polyene macrolide antibiotics and to the resultant purified chemotherapeutic compositions.

BACKGROUND OF THE INVENTION

Polyene macrolide antibiotics represent an important class of compounds which have found wide utility in the pharmaceutical field, especially because of their antibiotic properties. Many of the currently identified polyene macrolide antibiotics are illustrated in FIG. 26. The compounds are uniquely characterized by a large lactone ring which includes a chain of conjugated double bonds, comprising from three to seven such conjugated double bonds.

Although amphotericin B is the most well-known of the polyene macrolide antibiotics, other polyene antibiotics such as faeriefungin, nystatin, natamycin, hamycin, aureofungin and candicidin, have been known and used clinically for many years. More recently, dermostatin has been found to have activity against fungi and to be useful in the treatment of certain fungal infections.

The compounds are generally classified according to the number of conjugated double bonds in the structure and are correspondingly referred to as trienes, tetraenes, pentaenes, hexaenes and heptaenes, as illustrated in FIG. 26. The compounds all have high molecular weight, such as from about 700 to about 1200, and may be referred to as macrocyclic lactones, which have an amino sugar glycoside of a macrolide nucleus that possess a chromophore of 3 to 7 conjugated double bonds.

Because the polyene macrolide antibiotics conventionally are produced by cultivation of various organisms, it is often the case that they exist as complexes which contain more than one dominant macrolide structure. For example, dermostatin (or dermostatin complex) is known in actuality to contain two dominant structures which have been identified and named dermostatin A and dermostatin B. They are both carbonyl conjugated polyene macrolide antimicrobial agents that differ only slightly in structure. Heretofore, no preparatory procedure has existed to isolate dermostatin A and dermostatin B from the dermostatin complex in purified forms.

Similarly, mycoticin, it has now been discovered, is comprised of three distinct compounds now known as mycoticin A, mycoticin B and mycoticin C. There also has not been available a preparatory procedure for isolating and purifying those individuals components of mycoticin complex. A similar need for a general separation and purification procedure exists with respect to other polyene macrolide antibiotics as well.

SUMMARY OF THE INVENTION

It has now been discovered that polyene macrolide antibiotics can be separated into their major components and purified through a general preparatory procedure employing high pressure liquid chromatography. The procedure allows for the first time a general, efficacious method for separating the polyene macrolide complexes derived from fermentation and cultivation of various organisms, into their major components.

BRIEF DESCRIPTION OF THE FIGS.

FIG. 1 is a plot of the ultraviolet-visible spectrum for dermostatin complex in methanol.
FIG. 2 is a plot of the ultraviolet-visible spectrum for dermostatin A in methanol.
FIG. 3 is a plot of the ultraviolet-visible spectrum of dermostatin B in methanol.
FIG. 4 is a plot of the infrared spectrum for dermostatin complex.
FIG. 5 is a plot of the infrared spectrum for dermostatin A.
FIG. 6 is a plot of the infrared spectrum for dermostatin B.
FIG. 7 is a high performance liquid chromatogram for dermostatin complex.
FIG. 8 is a high performance liquid chromatogram for dermostatin A.
FIG. 9 is a high performance liquid chromatogram for dermostatin B.
FIG. 10A is a structural formula for Dermostatin A;
FIG. 10B is a thermospray negative ion mass spectrum or dermostatin A.
FIG. 11A is the structural formula for Dermostatin B;
FIG. 12 is the structural formula for dermostatin A.
FIG. 13 is the structural formula for dermostatin B.
FIG. 14 is a plot of the ultraviolet-visible spectrum for mycoticin complex in methanol.
FIG. 15 is a plot of the ultraviolet-visible spectrum for mycoticin A in methanol.
FIG. 16 is a plot of the ultraviolet-visible spectrum of mycoticin B in methanol.
FIG. 17 is a plot of the infrared spectrum for mycoticin complex.
FIG. 18 is a plot of the infrared spectrum for mycoticin A.
FIG. 19 is a plot of the infrared spectrum for mycoticin B.
FIG. 20 is a high performance liquid chromatogram for mycoticin complex.
FIG. 21 is a high performance liquid chromatogram for mycoticin A.
FIG. 22 is a high performance liquid chromatogram for mycoticin B.
FIG. 23A is a structural formula for mycoticin A.
FIG. 23 is a thermospray negative ion mass spectrum for mycoticin A.
FIG. 24A is a structural formula for mycoticin B;
FIG. 24B is a thermospray negative ion mass spectrum for mycoticin B.
FIG. 25 is the structural formula for mycoticin A (when $R=CH_3$) and mycoticin B (when $R=CH_2CH_3$).
FIG. 26 is a chart showing various polyene macrolide antibiotics, characterized based upon structure.
FIG. 27 is a high performance liquid chromatogram for mycoticin complex, labeled to show the presence of newly identified mycoticin C.
FIG. 28A is a structural formula for mycoticin C.
FIG. 28B is a thermospray negative ion mass spectrum for mycoticin C.

DETAILED DESCRIPTION OF THE PREFERRED EMBODIMENTS

Figure 1:
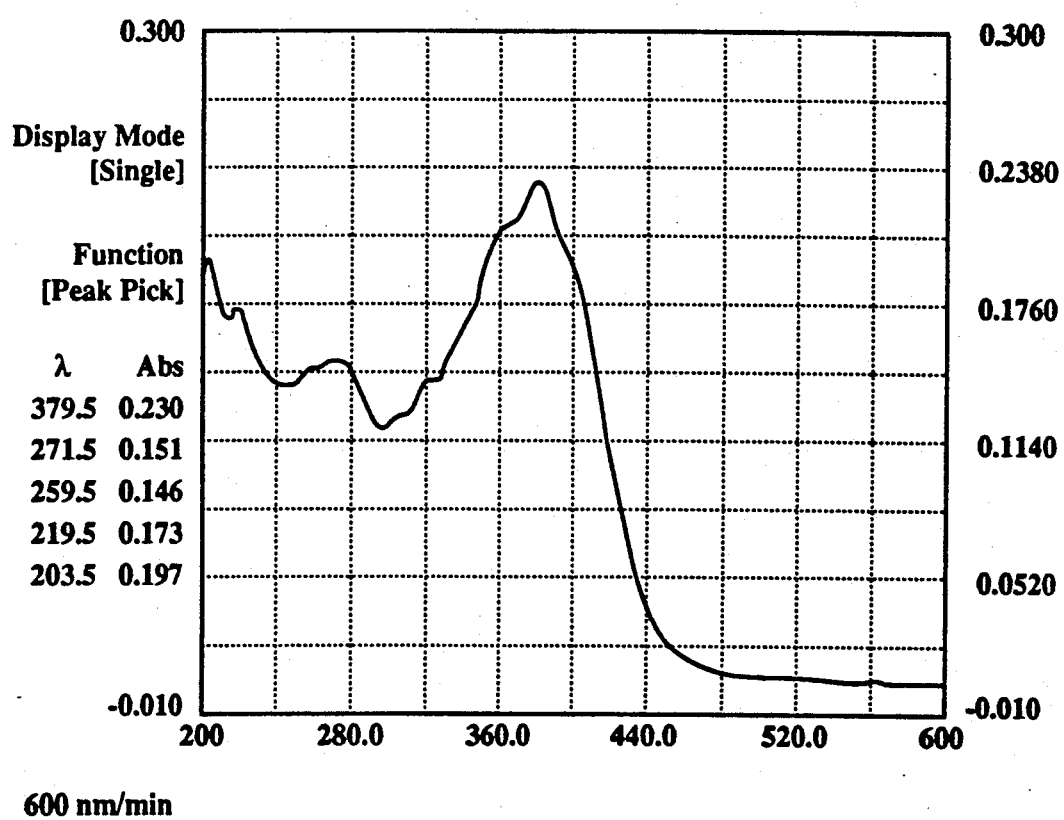

In accordance with the present invention, polyene macrolide complexes may be separated into their components and purified to produce high-purity compositions. The complex is separated by use of a specific separation procedure which comprises dissolving the complex in a solvent for the complex at any suitable concentration, such as from about 1 to about 100 mg of complex per milliliter of solvent. The solution is then injected, in aliquots, into a suitable separation column, using an isocratic solvent system, such as methanol-water as the mobile phase. If methanol-water is used as the mobile phase, the methanol-water ratio may range from about 60 parts of methanol per 40 parts of water to about 80 parts of methanol per 20 parts of water. A typical flow rate of from about 10 to about 20 ml per minute is suitable, about 14 ml per minute being preferred. The detection for the elution of each component is followed at approximately the frequency at which the maximum absorption is exhibited for the desired constituents and as the peak is detected, fractions are collected. The fractions are then analyzed to determine the chemical identity of the fractions. The fractions with identical retention times are then combined and concentrated, as by rotary evaporation, and the resulting precipitate is filtered and dried.

As indicated, in accordance with the present invention, dermostatin (also known as dermostatin complex) which contains both dermostatin A and dermostatin B has been separated into its components to produce high-purity dermostatin A and dermostatin B, which heretofore has not been available. The dermostatin complex is separated bY use of a specific separation procedure which comprises dissolving the dermostatin complex in dimethylsulfoxide (DMSO) at any suitable concentration, such as from about 1 to about 100 mg dermostatin per milliliter of DMSO, preferably about 20 mg/ml. The solution is then injected, in aliquots, into a suitable separation column, using an isocratic solvent system of methanol-water as the mobile phase. The methanol-water ratio may range from about 60 parts of methanol per 40 parts of water to about 80 parts of methanol per 20 parts of water. Preferably, the methanol-water ratio is about 74:26. A typical flow rate of from about 10 to about 20 ml per minute is suitable, about 14 ml per minute being preferred. The detection for the elution of each component is followed at 390 nm and as the peak is detected, 50 ml or other suitably sized fractions are collected. The fractions are then analyzed to identify the fractions which are dermostatin A and dermostatin B, respectively. The fractions with identical retention times are then combined and concentrated, as by rotary evaporation, and the resulting precipitate is filtered and dried. When using a Waters Delta Pak $C_{18}$ column (19×300 mm, 100 angstrom, 15 micron particle size) the fraction having a retention time of 9.92 minutes is the dermostatin A fraction and the fraction having a retention time of 14.36 minutes is the dermostatin B fraction.

Figure 2:
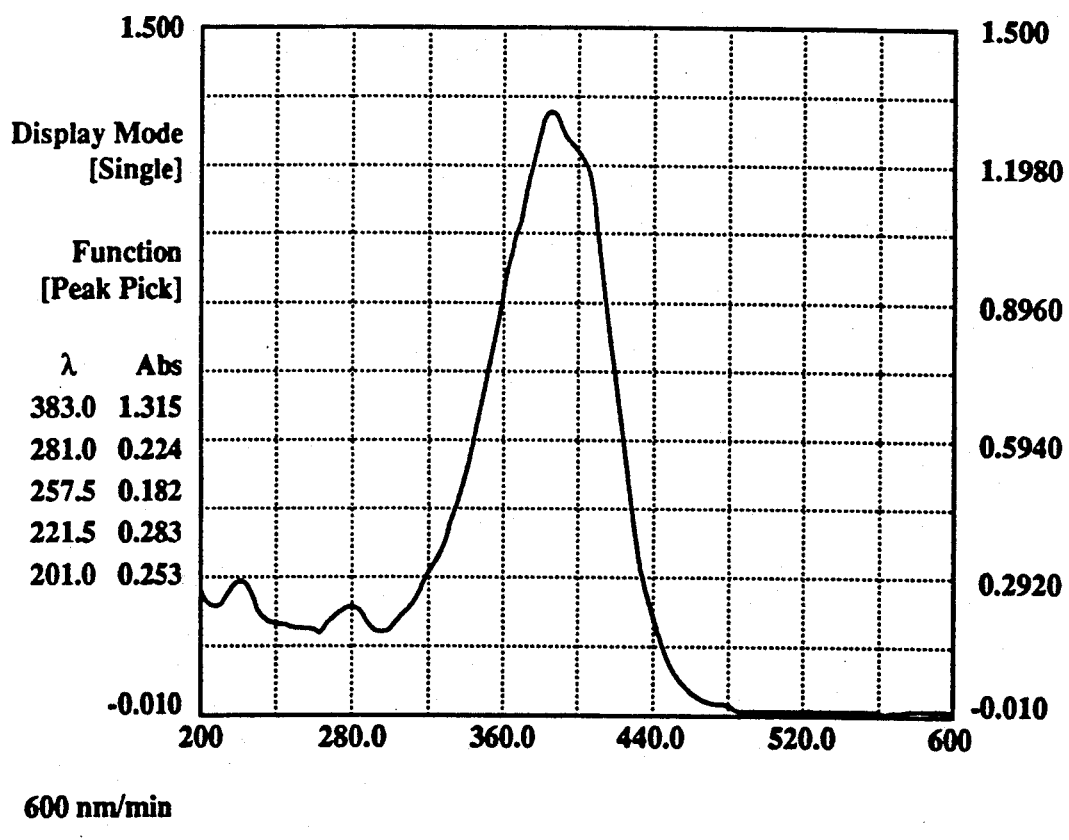
Figure 3:
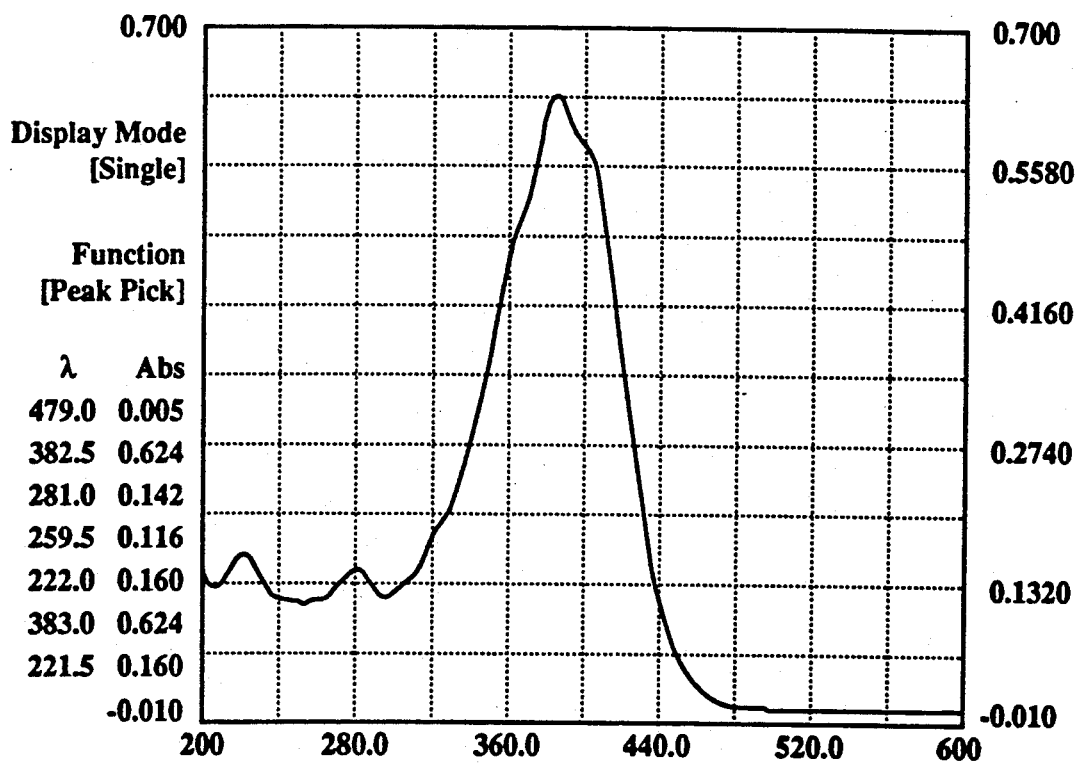
Figure 10A:
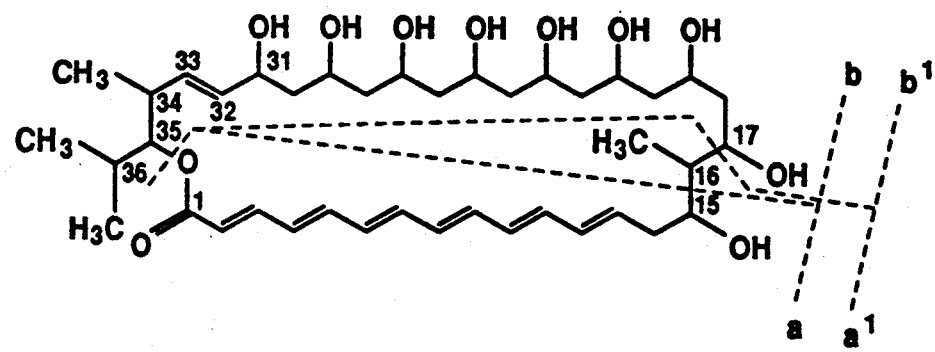
Figure 11A:
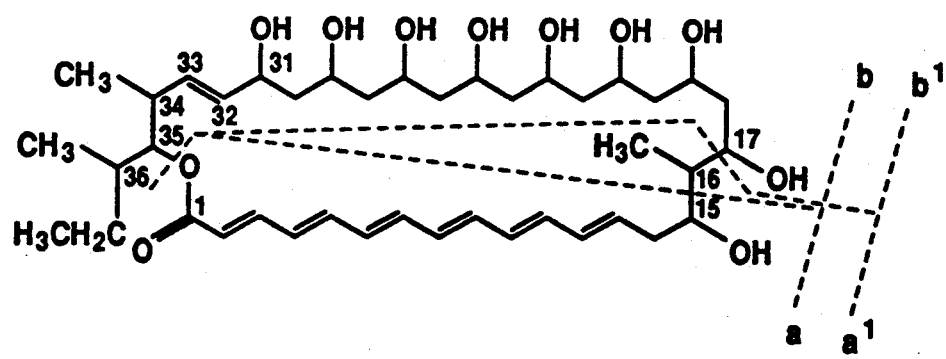
Figure 10B:
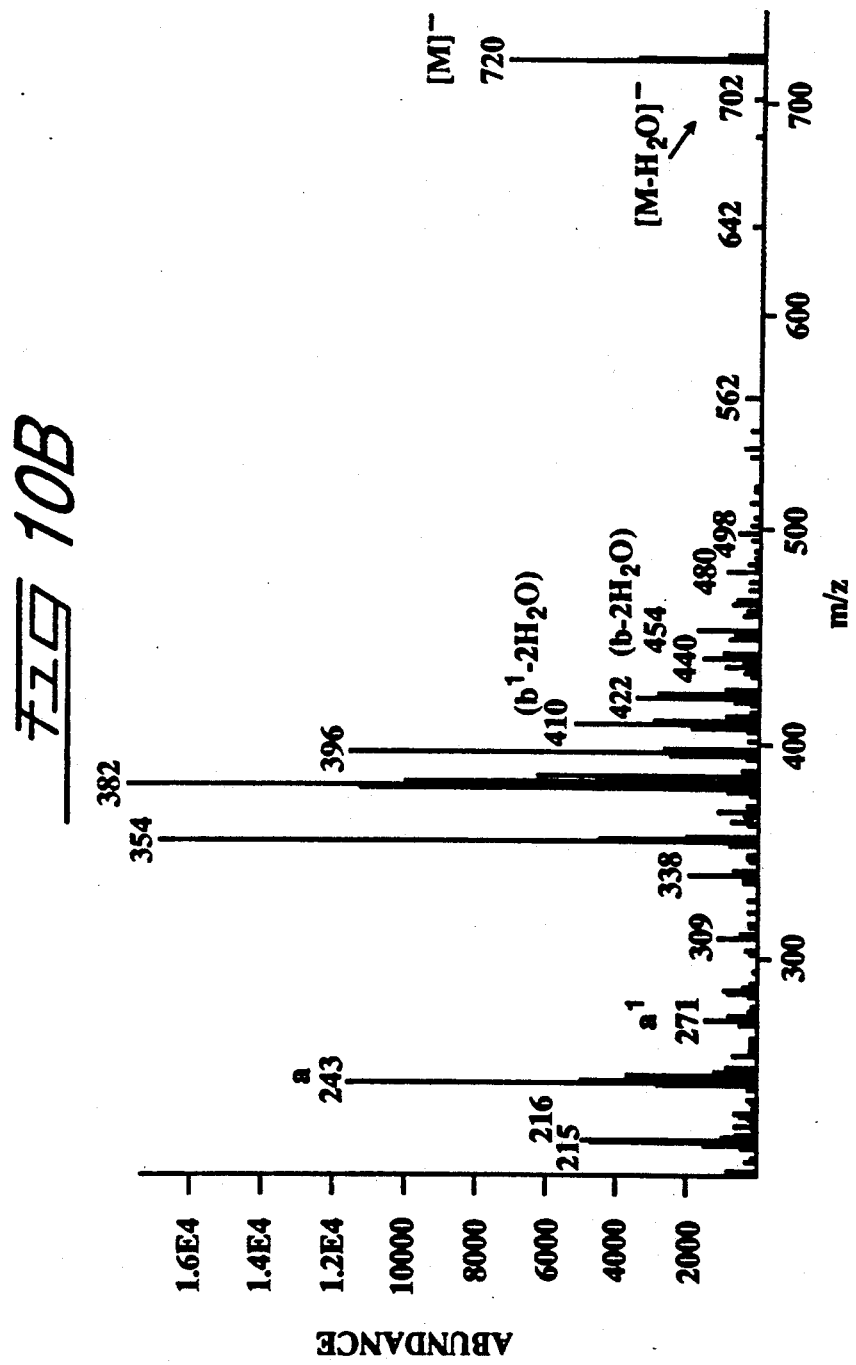
Figure 12:
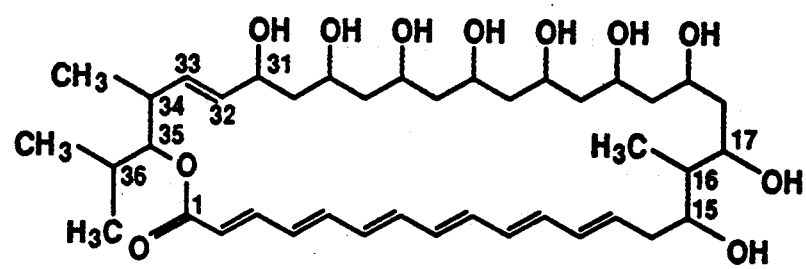
Figure 13:
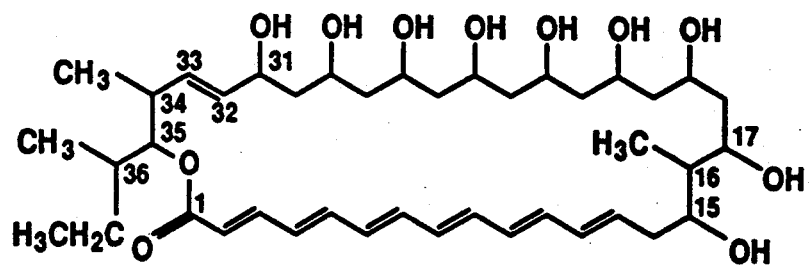

The properties of dermostatin complex, dermostatin A and dermostatin B are summarized in Tables I-III, their respective uv-vis spectra are shown in FIGS. 1-3, their respective IR spectra are shown in FIGS. 4-6 and their respective HPLC plots are shown in FIGS. 7-9. The respective thermospray negative ion mass spectra are shown in FIGS. 10-11, for dermostatin A and dermostatin B and their respective structures are shown in FIGS. 12 and 13.

Also, in accordance with the present invention, mycoticin complex may be separated into its components. The mycoticin is first dissolved in a solvent, such as a methanol water mixture (74:26), which also may serve as the mobile phase. The mycoticin may be dissolved at any suitable concentration, such as from about 2 to about 4 mg of mycoticin per ml of solvent, preferably, about 71 mg mycoticin per 20 milliliters of mobile phase. The solution may then be injected in suitable aliquots, such as 20 ml at a time, through a solvent line into a suitable preparatory separation column. A Waters Delta Pak $C_{18}$ column (19×300 mm, 100 angstrom, 15 micron particle size) is preferred.

A methanol-water solvent system is preferred as the mobile phase, preferably wherein the methanol-water ratio is from about 60 parts of methanol to 40 parts of water to about 80 parts of methanol to 20 parts of water, with a ratio of about 74:26 being preferred. The mobile phase may have any suitable flow rate, such as from about 10 to about 20 ml per minute, with a flow rate of 11 ml per minute being preferred. Chart sensitivity and speed preferably are adjusted to 10 AUFS and 0.25 cm/minute, respectively.

The detection for the elution of each component may be followed at about 300 nm. As a peak is detected, appropriate sized fractions, such as approximately 25 ml, may be collected. The fractions may then be checked by analytical HPLC, as on a Waters Nova Pak $C_{18}$ column (3.9×150 mm, using methanol-water (74:26) as the mobile phase at a flow rate of 1.5 ml/min, and an injection volume of 20 microliters, with detection at UV-Vis, 300 nm). The fractions having identical retention time, which is approximately 6.05 minutes on the preferred column, will be the mycoticin A fraction and the fractions having a retention time of approximately 8.57 minutes, using the preferred column will be the mycoticin B fraction.

The fractions with identical retention times may then combined and a solvent added, if desired, such as 1-butanol. The mixtures may be suitably concentrated, as by rotary evaporation at about 45 degrees C, to a small volume and the resulting precipitate may be recovered, as by filtering and drying.

Figure 14:
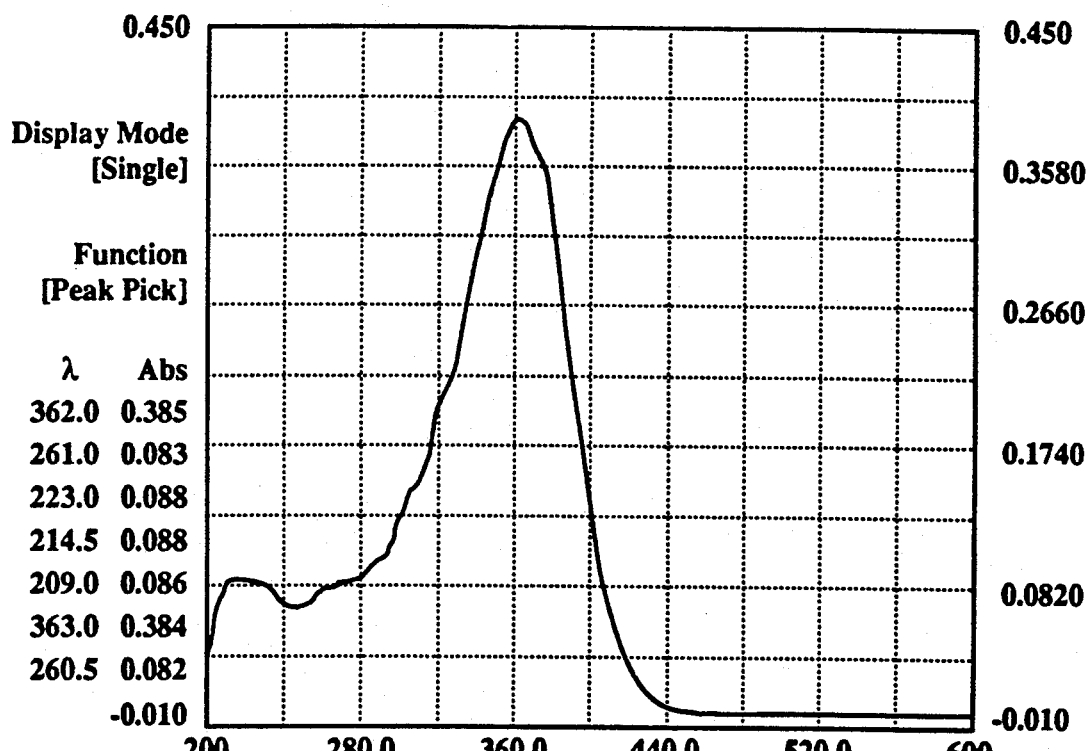
Figure 15:
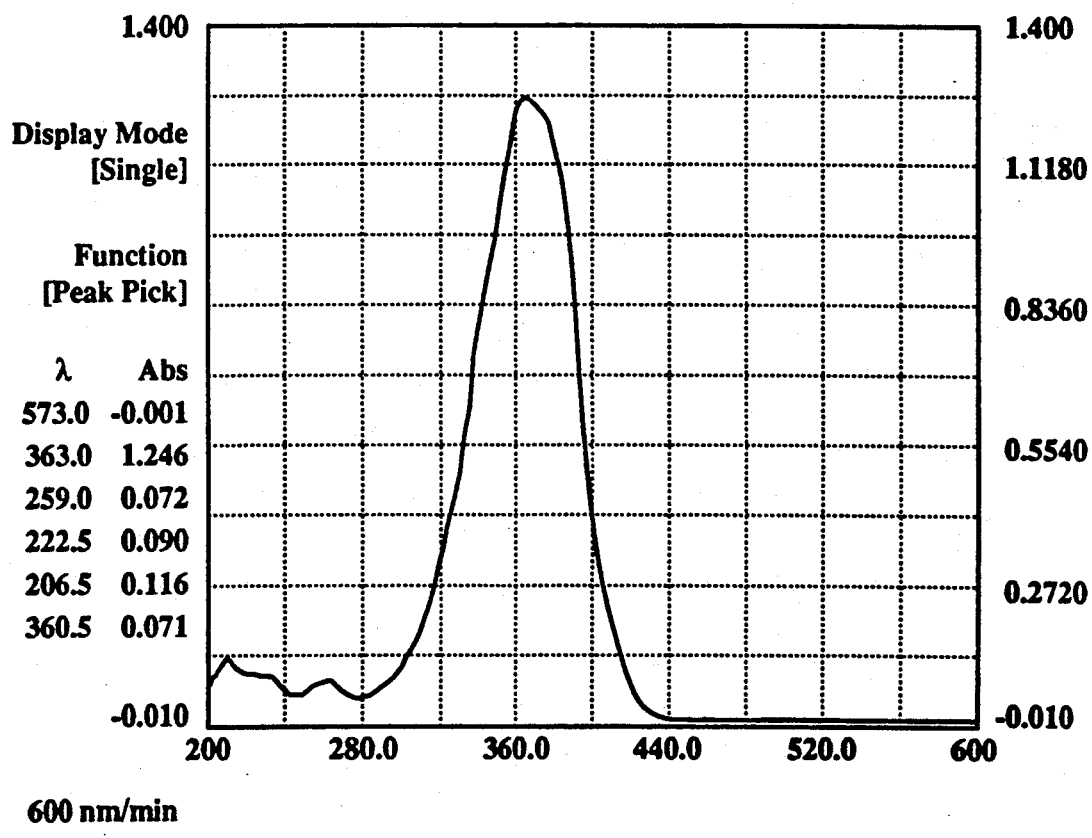
Figure 16:
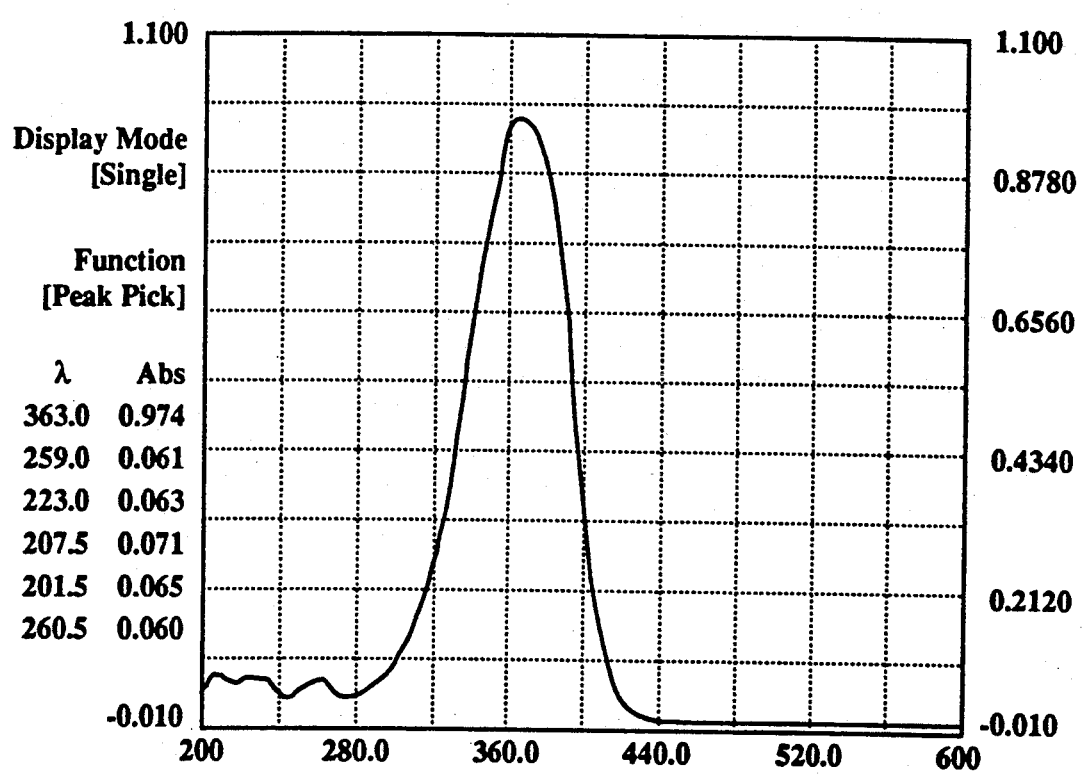
Figure 17:
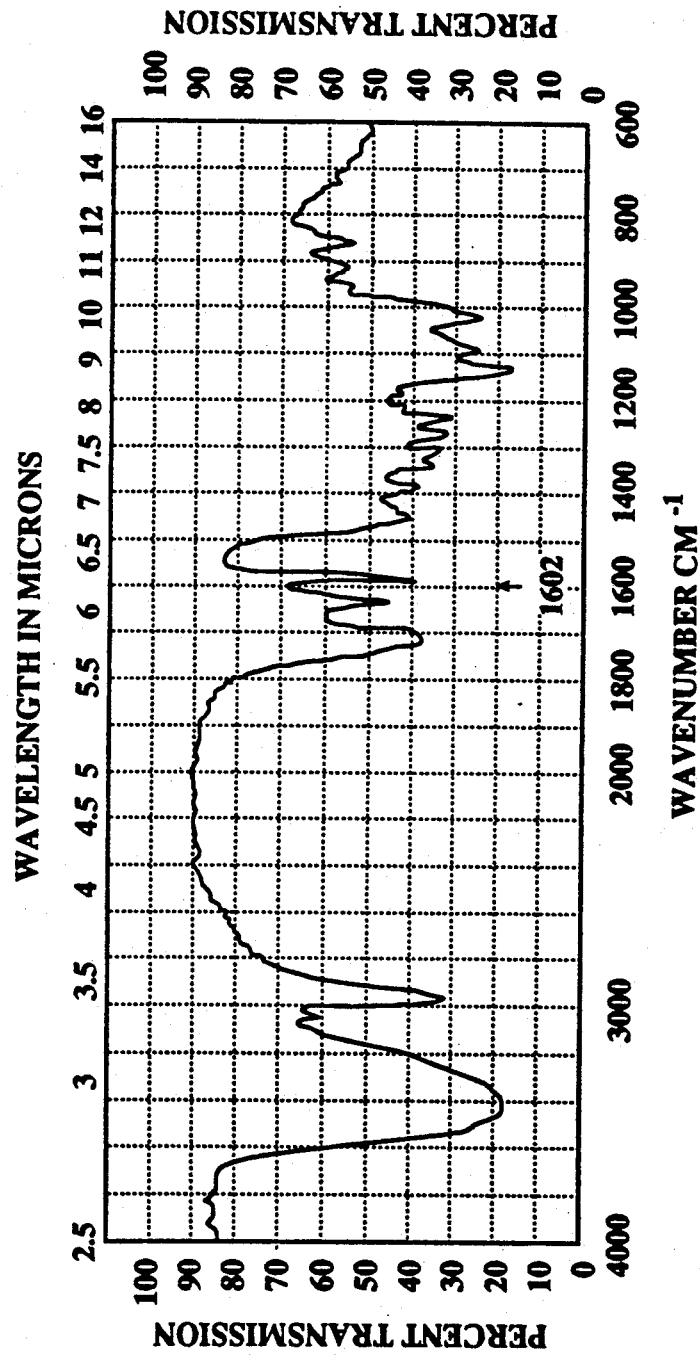
Figure 18:
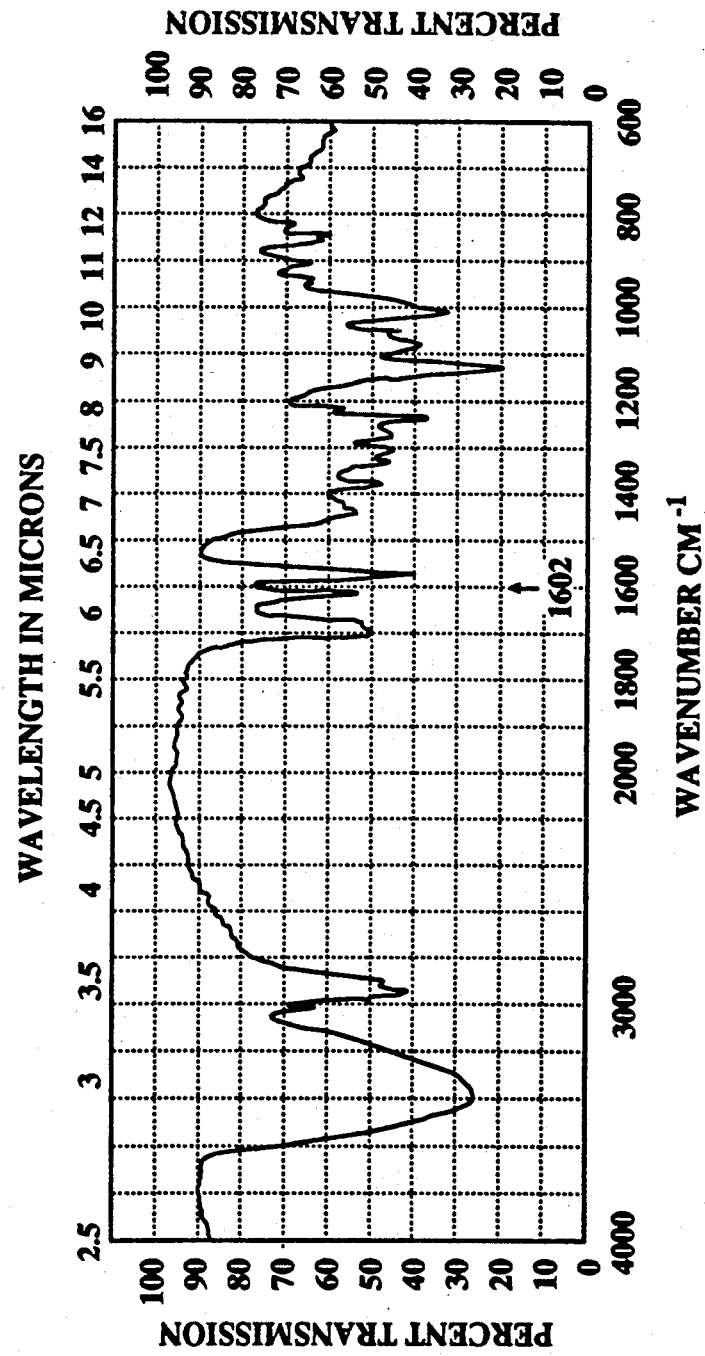
Figure 19:
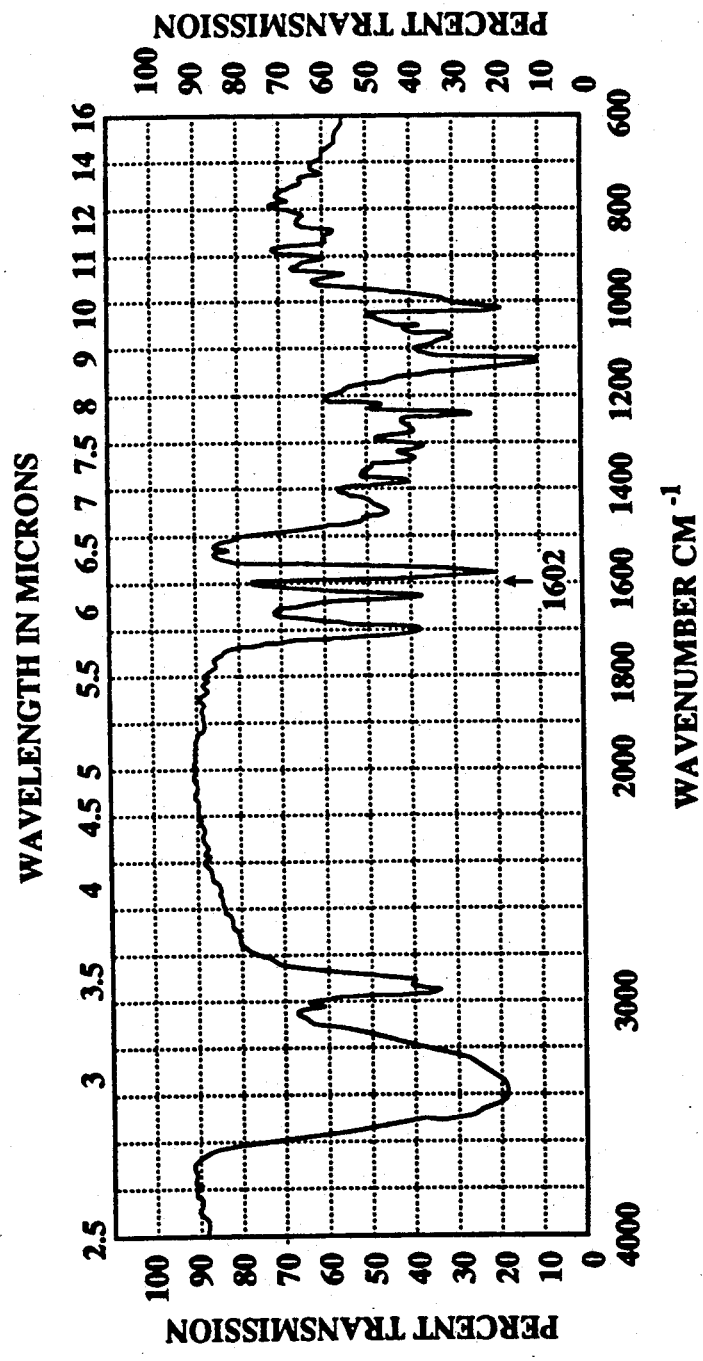
Figure 20:
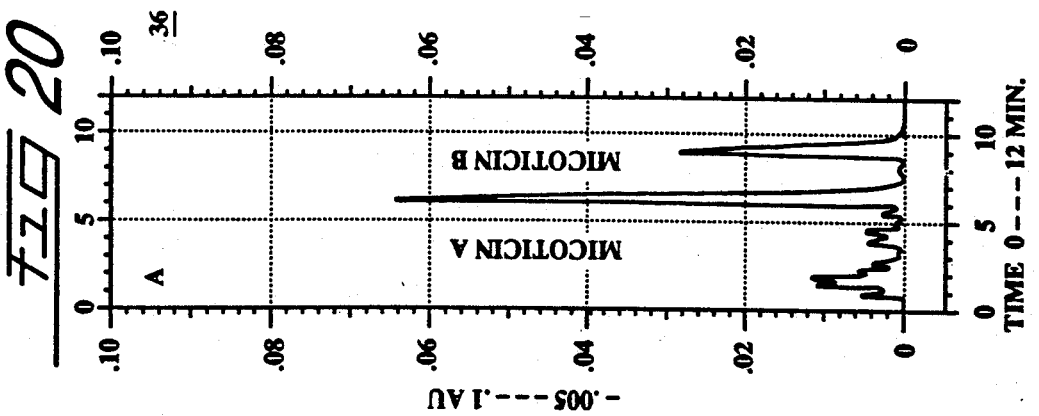
Figure 21:
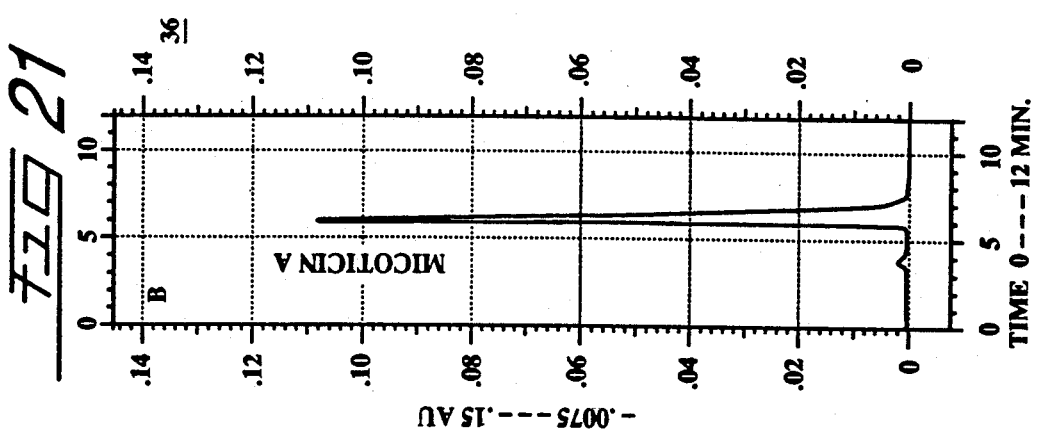
Figure 22:
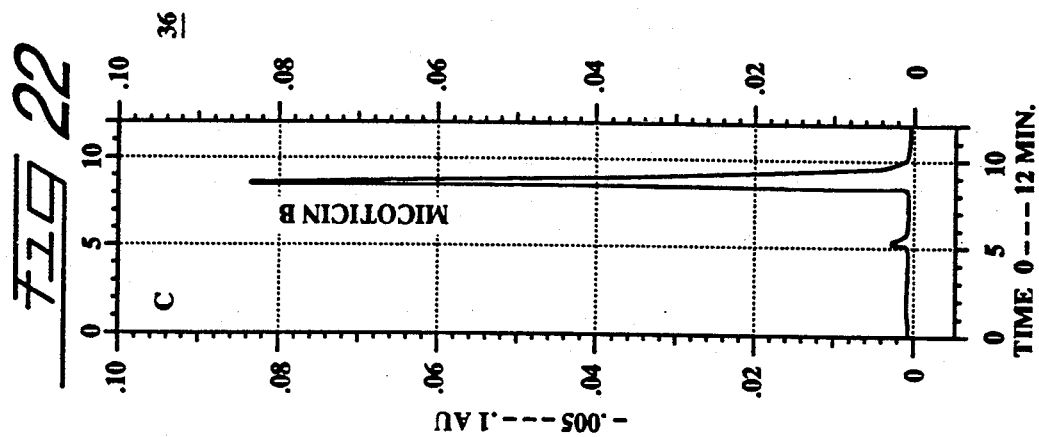
Figure 23A:
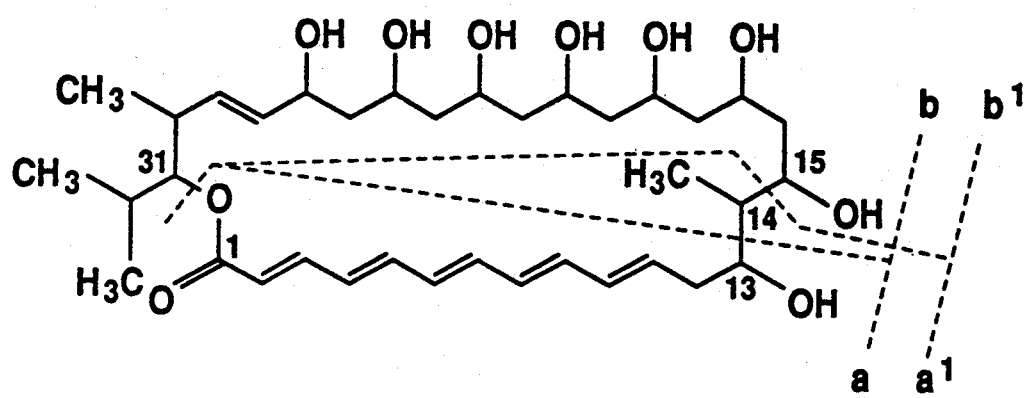
Figure 24A:
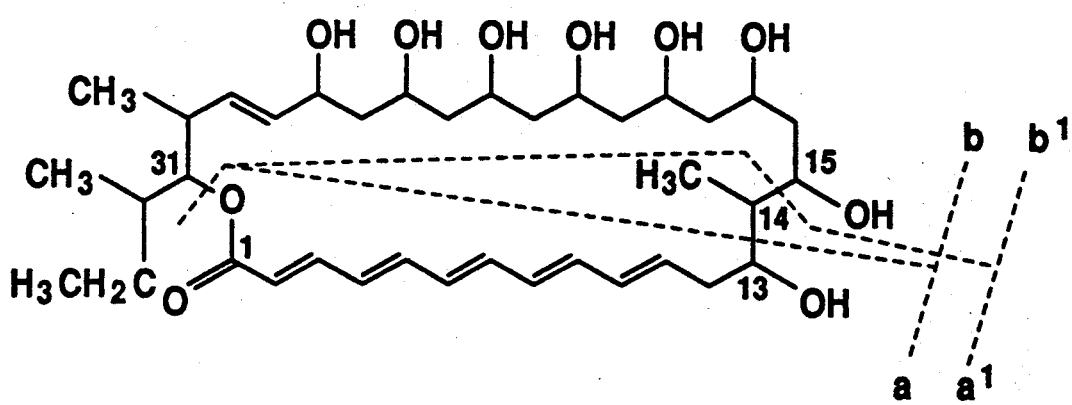
Figure 23B:
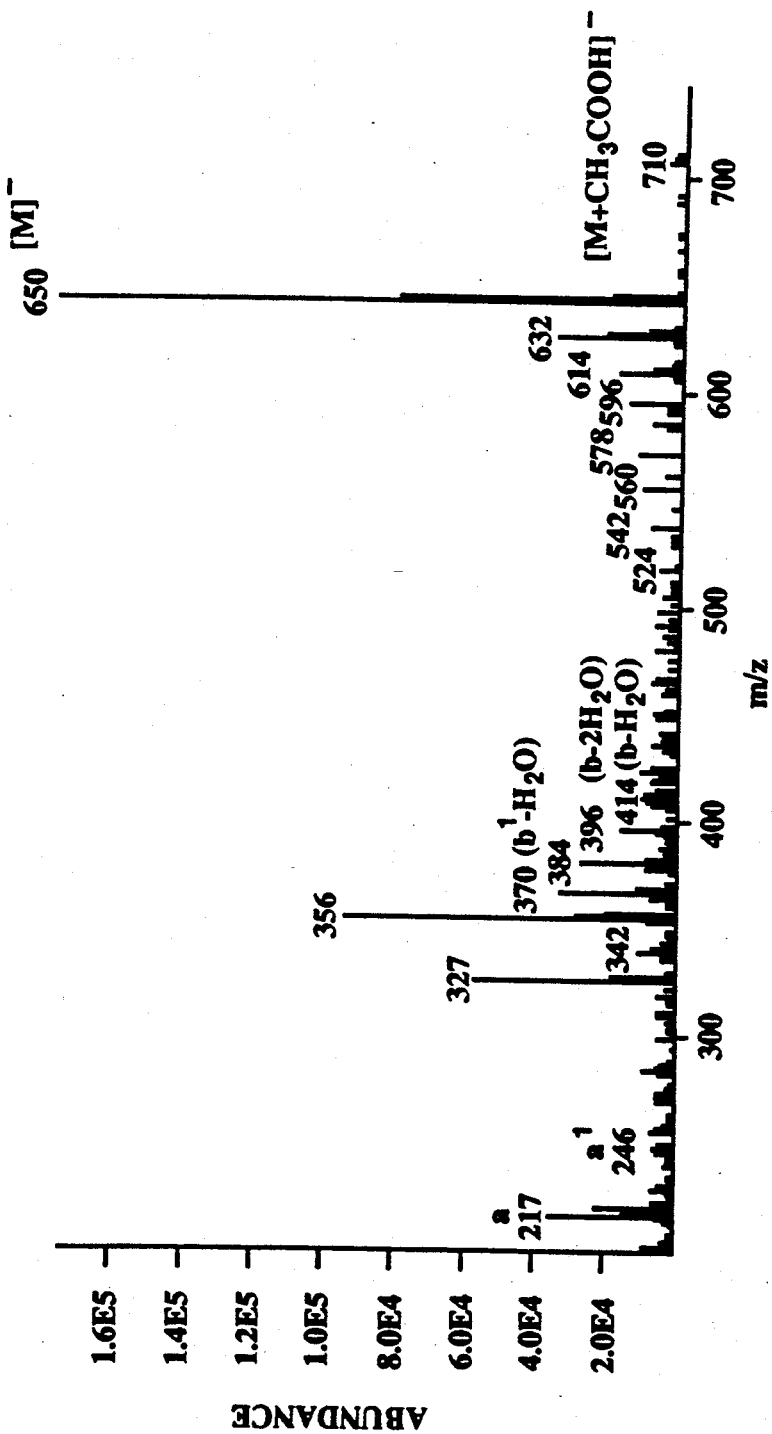
Figure 24B:
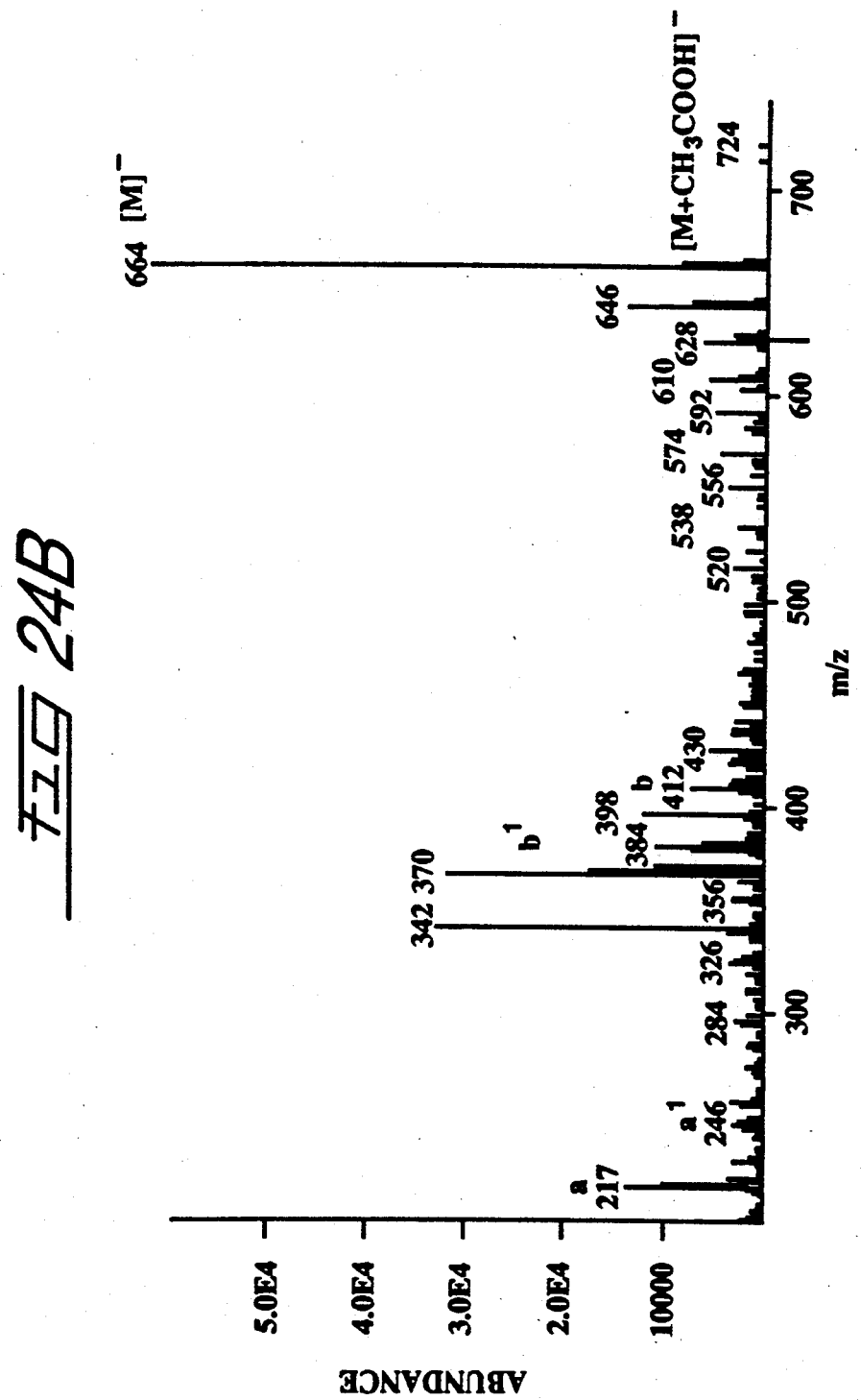
Figure 25:
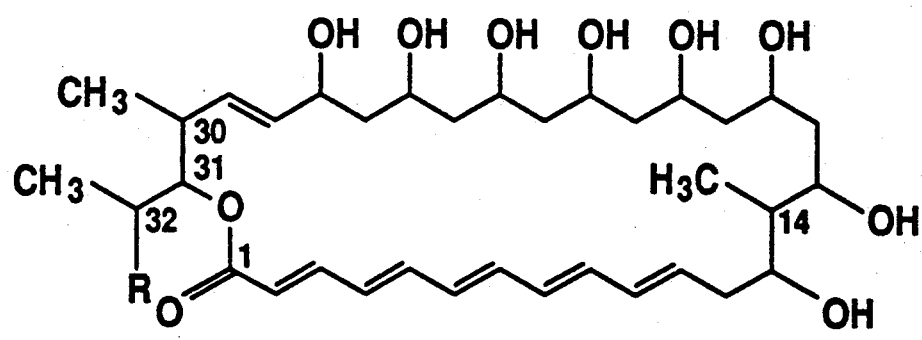
Figure 26:
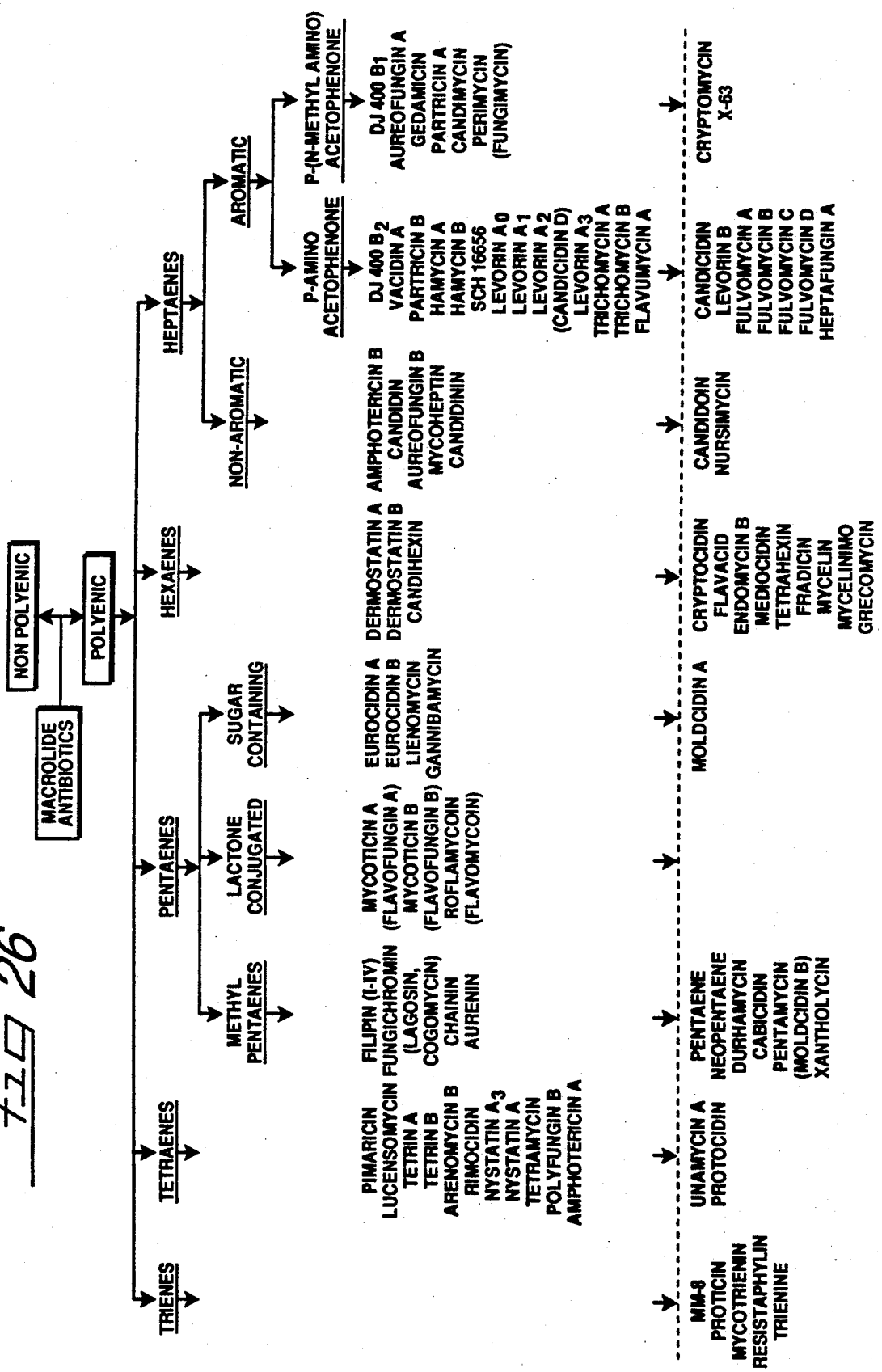

The properties of mycoticin complex, mycoticin A and mycoticin B are summarized in Tables IV-VI, their respective uv-vis spectra are shown in FIGS. 14-16, their respective IR spectra are shown in FIGS. 17-19 and their respective HPLC plots are shown in FIGS. 20-22. The respective thermospray negative ion mass spectra are shown in FIGS. 23≧24, for mycoticin A and mycoticin B and their respective structures are shown in FIG. 25.

Figure 28A:
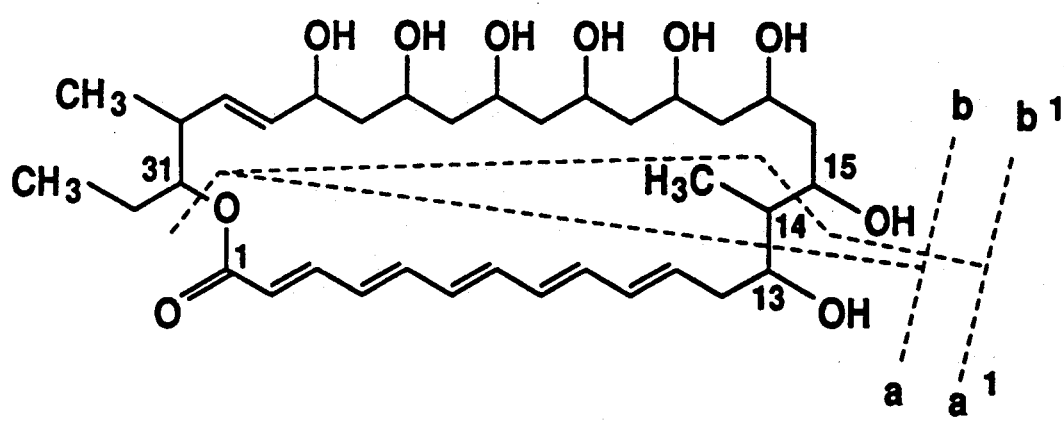
Figure 28B:
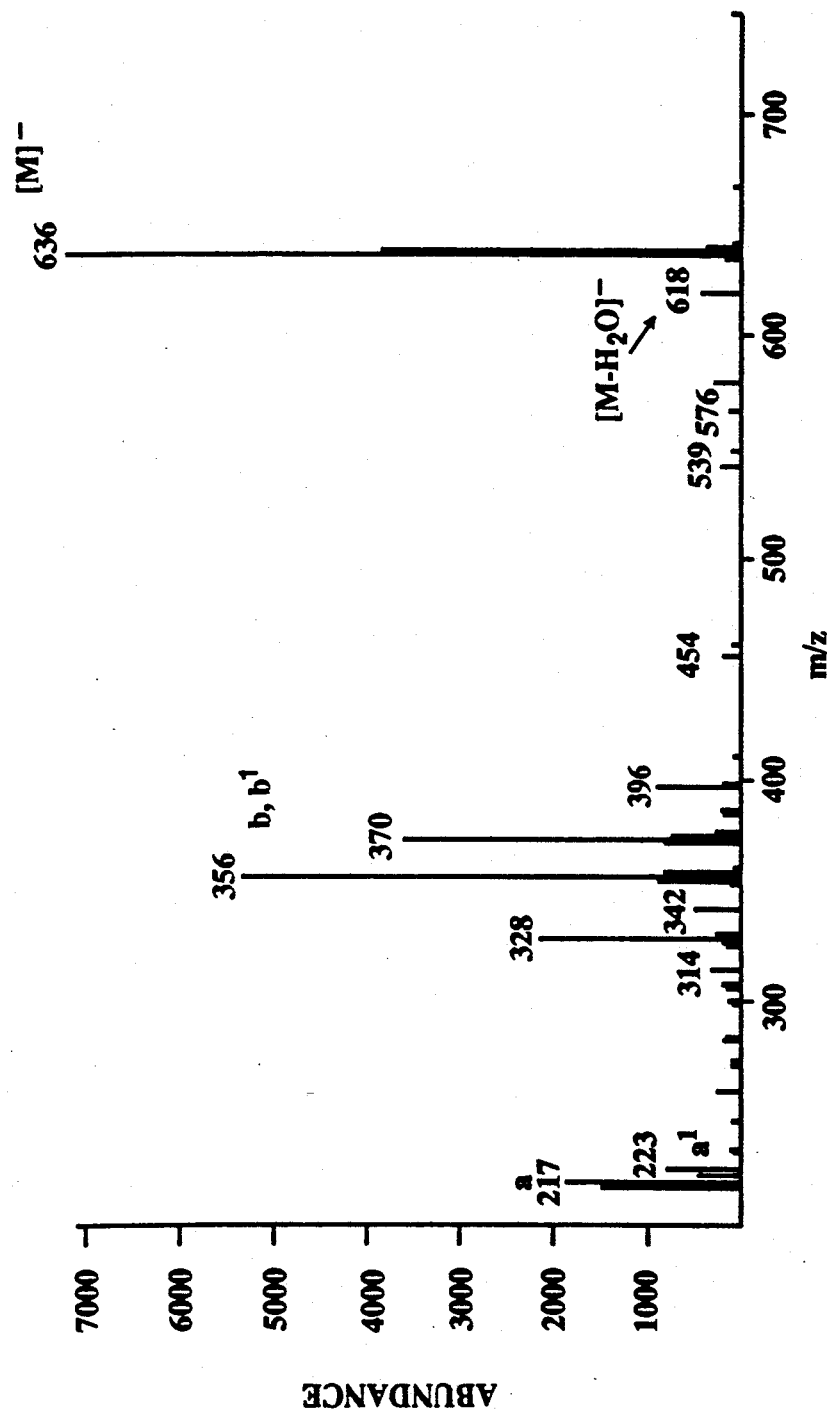

It has now also been discovered that mycoticin complex contains a third major component, now identified as mycoticin C. FIG. 27 is a high performance liquid chromatogram for mycoticin complex, labeled to show the earlier eluting mycoticin C component. The thermospray negative ion mass spectrum of mycoticin C is shown in FIG. 28.

The components recovered by virtue of the separation procedure of the present invention have purities of at least about 90 percent, preferable at least about 95% and most preferably at least about 99 percent. The purified product can be dissolved in any pharmaceutically acceptable carrier, such as water, saline solution, or dextrose solution (5%).

The separated, purified polyene macrolide antibiotics derived from the process of the present invention may be administered to the patient in any suitable form. It will be appreciated by those skilled in the art that many generally accepted delivery methods or forms have the potential of being similarly efficacious, such as emulsions, liposomal encapsulated formulations, various oral dosage forms, attachment of the drug to monoclonal antibodies specific to certain target antigens, metal complexes or chelates, or pro-drugs which generate the active compound in vivo. The exact manner by which the antibiotic is administered to the patient is not critical, so long as the desired concentration of the antibiotic is achieved. In some instances, it may be possible to develop controlled release formulations of antibiotic which will maintain the desired concentration of antibiotic within the patient over prolonged periods of time. Such devices may include implants, transdermal patches, and the like. The exact manner of administration is not critical.

EXAMPLES

Example 1

Separation and Purification of Dermostatin A and Dermostatin B from Dermostatin Complex Dermostatin complex was dissolved in dimethylsulfoxide (DMSO) at a concentration of 20 mg dermostatin per milliliter of DMSO. The solution was then injected, 5 ml at a time, through a solvent line into a Waters Delta Pak $C_{18}$ column (19×300 mm, 100 angstrom, 15 micron particle size), using an isocratic solvent system of methanol-water (74:26) as the mobile phase at a flow rate of 14 ml per minute. Chart sensitivity was adjusted to 1.0 AUFS and chart speed to 0.25 cm/minute. The detection for the elution of each component was followed at 390 nm and as the peak was detected, 50 ml fractions were collected. The fractions were checked by analytical HPLC on a Waters Nova Pak $C_{18}$ column (3.9×150 nm, using methanol-water (74:26) as the mobile phase at a flow rate of 1.5 ml/min, and an injection volume of 10 microliters, with detection at UV-Vis, 390 nm. The fractions having a retention time of 9.92 minutes were determined to be the dermostatin A fraction and the fractions having a retention time of 14.36 minutes were determined to be the dermostatin B fraction. The fractions with identical retention times were then combined and each concentrated by rotary evaporation at about 30 degrees C., to a small volume of approximately 5 ml. and the resulting precipitate filtered and dried to form a golden yellow amorphous powder.

The dermostatin A fractions which eluted at 9.92 minutes had a melting point of 135°–139 degrees C and the dermostatin B fractions which eluted at 14.36 minutes had a melting point of 138–144 degrees C. Further analytical information regarding the original dermostatin complex and the purified compounds is set forth in Tables I–III and FIG. 1–11.

Example 2

Separation and Purification of Mycoticin A and Mycoticin Complex

Mycoticin complex was dissolved in a methanol Water mixture (74:26) which also served as the mobile phase. The mycoticin was dissolved at a concentration of 71 mg mycoticin per 20 milliliter of mobile phase. The solution was then injected, 20 ml at a time, through a solvent line into a Waters Delta Pak $C_{18}$ column (19×300 mm, 100 angstrom, 15 micron particle size), using the isocratic solvent system of methanol-water (74:26) as the mobile phase at a flow rate of 11 ml per minute. Chart sensitivity was adjusted to i.e. AUFS and chart speed to 0.25 cm/minute. The detection for the elution of each component was followed at 300 nm and as the peak was detected, approximately 25 ml fractions were collected. The fractions were checked by analytical HPLC on a Waters Nova Pak $C_{18}$ column (3.9×150 mm, using methanol-water (74:26) as the mobile phase at a flow rate of 1.5 ml/min, and an injection volume of 20 microliters, with detection at UV-Vis, 300 nm. The fractions having a retention time of approximately 6.05 minutes were determined to be the mycoticin A fraction and the fractions having a retention time of approximately 8.57 minutes were determined to be the mycoticin B fraction. The fractions with identical retention times were then combined and 100 ml of 1-butanol added. The mixtures were then concentrated by rotary evaporation at about 45 degrees C, to a small volume and the resulting precipitate filtered and dried overnight under vacuum to form a golden yellow amorphous powder.

The mycoticin A fractions which eluted at approximately 6.05 minutes had a melting point of 126–130 degrees C and the mycoticin B fractions which eluted at 8.57 minutes had a melting point of 124–31 degrees C. Further analytical information regarding the original mycoticin complex and the purified compounds is set forth in Tables IV–VI and FIGS. 15–25.

It was also found that a third mycoticin component, mow referred to as mycoticin C, exists and elutes earlier than the two previously known variations of mycoticin, as shown in FIG. 27, which is a high pressure liquid chromatograph taken with a Waters Nova-Pak $C_{18}$ (3.9 mm×150 mm, 5 micron) column, using a methanol-water (74:26) mobile phase, at a flow rate of 1.5 ml/minute, with detection at 360 nm. A thermospray negative ion mass spectrum, along with the structure of mycoticin C determined thereby, is shown in FIG. 28.

TABLE I

| Physicochemical Properties of Dermostatin Complex | |
|---|---|
| Nature: | Golden yellow amorphous powder |
| Mol. Formula: | $C_{40}H_{64}O_{11}$ (24%; $C_{41}H_{66}O_{11}$ (34%) |
| Mol. Wt: | $C_{40}H_{64}O_{11}$, 720; $C_{41}H_{66}O_{11}$, 734 |
| Melting Point: | 142–146° C. |
| TLC* (Rf): | 0.63 ± 0.02 |
| HPLC** (RT): | $C_{40}H_{64}O_{11}$, 9.92 min; $C_{41}H_{66}O_{11}$, 14.36 min FIG. 7 |
| Solubility: | Soluble in MeOH, DMSO, DMF Insoluble in $H_2O$, pet ether, hexane |
| UV-Vis (MeOH): | FIG. 1 |
| IR (KRr pellet): | FIG. 4 |

*Plates: Silica Gel 60, F254 (20 × 20 cm, 250 thickness);
Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 390 nm

TABLE II

| Physicochemical Properties of Demostatin A | |
|---|---|
| Nature: | Golden yellow amorphous powder |
| Mol. Formula: | $C_{40}H_{64}O_{11}$ |
| Mol. Wt: | 720 |
| Melting Point: | 135–139° C. |
| TLC* (Rf): | 0.63 ± 0.02 |
| HPLC** (RT): | 9.92 min FIG. 8 |
| Solubility: | Soluble in MeOH, DMSO, DMF Insoluble in $H_2O$, pet ether, hexane |
| UV-VIS (MeOH): | λ max (ε) 383.0 (47,406); 81.0 nm (8,075) FIG. 2 |
| ISR (KBr pellet): | FIG. 5 |

*Plates: Silica Gel 60, F254 (20 × 20 cm, 250 thickness);
Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 390 nm

TABLE III

Physicochemical Properties of Dermostatin B

| | |
|---|---|
| Nature: | Golden yellow amorphous powder |
| Mol. Formula: | $C_{40}H_{64}O_{11}$ |
| Mol. Wt: | 734 |
| Melting Point: | 138–144° C. |
| TLC* (Rf): | 0.64 ± 0.02 |
| HPLC** (RT): | 14.36 min FIG. 9 |
| Solubility: | Soluble in MeOH, DMSO, DMF |
| | Insoluble in $H_2O$, pet ether, hexane |
| UV-Vis (MeOH): | λ max (ε) 383.0 (19,859); 281.0 nm (4,519) |
| | FIG. 3 |
| IR (KBr pellet): | FIG. 6 |

*Plates: Silica Gel 60, F254 (20 × 20 cm, 250 thickness);
Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 390 nm

TABLE IV

Physicochemical Properties of Dermostatin Complex

| | |
|---|---|
| Nature: | Pale yellow crystalline needles |
| Mol. Formula: | $C_{36}H_{58}O_{10}$ (52%); $C_{37}H_{60}O_{10}$ (31%) |
| Mol. Wt: | $C_{36}H_{58}O_{10}$. 650; $C_{37}H_{60}O_{10}$. 664 |
| Melting Point: | 133–137° C. |
| TLC* (Rf): | 0.69 ± 0.01 (FIG. 1A) |
| HPLC** (RT): | $C_{36}H_{58}O_{10}$, 6.05 min; $C_{37}H_{60}O_{10}$, 8.57 min (FIG. 2A) |
| Solubility: | Soluble in MeOH, DMSO, DMF |
| | Insoluble in $H_2O$, pet ether, hexane |
| UV-Vis (MeOH): | FIG. 3A |
| IR (KBr pellet): | FIG. 6A |

*Plates: Silica Gel 60, F254 (20 × 20 cm, 350 thickness);
Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 360 nm

TABLE V

Physicochemical Properties of Mycoticin A

| | |
|---|---|
| Nature: | Pale yellow amorphous powder |
| Mol. Formula: | $C_{36}H_{58}O_{10}$ |
| Mol. Wt: | 650 |
| Melting Point: | 126–130° C. |
| TLC* (Rf): | 0.69 ± 0.02 (FIG. 1A) |
| HPLC** (RT): | 6.05 (FIG 2A) |
| Solubility: | Soluble in MeOH, DMSO, DMF |
| | Insoluble in $H_2O$, pet ether, hexane |
| UV-Vis (MeOH): | λ max (ε) 363.0 (57,850); 260.5 nm (3,296) (FIG. 4A) |
| IR (KBr pellet): | FIG. 7A |

*Plates: Silica Gel 60, F254 (20 × 20 cm, 250 thickness);
Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 360 nm

TABLE VI

Physicochemical Properties of Mycoticin B

| | |
|---|---|
| Nature: | Pale yellow amorphous powder |
| Mol. Formula: | $C_{37}H_{60}O_{10}$ |
| Mol. Wt: | 664 |
| Melting Point: | 124–131° C. |
| TLC* (Rf): | 0.69 ± 0.03 (Fig. 1A) |
| HPLC** (RT): | 8.57 (Fig. 2A) |
| Solubility: | Soluble in MeOH, DMSO, DMF |
| | Insoluble in $H_2O$, pet ether, hexane |
| UV-Vis (MeOH): | λ max (ε) 363.0 (53,895); 260.5 nm (3,320) (FIG. 5A) |
| IR (KBr pellet): | Fig. 8A |

*Plates: Silica Gel 60, F254 (20 × 20 cm, 250 thickness);
Solvent System: n-Butanol-Acetic Acid-Water (4:1:5, upper layer)
**Column: Nova Pak $C_{18}$ (3.9 × 150 mm); Solvent System: Methanol-Water (74:26); Flow Rate: 1.5 ml/min; Detection: 360 nm

I claim:

1. A high pressure liquid chromatography method for producing substantially pure dermostatin A and dermostatin B comprising dissolving dermostatin complex in dimethylsulfoxide at a concentration from about 1 to about 100 mg of dermostatin per milliliter of dimethylsulfoxide; injecting the solution into a suitable separation column, using an isocratic solvent system of methanol and water as the mobile phase at a flow rate of from about 10 to about 20 ml per minute; detecting the absorption of the effluent at 390 nm and as a fraction having absorption at 390 nm is detected, recovering said fraction; combining the fractions with identical retention times; concentrating the combined fractions; and recovering the resultant precipitate.

2. A high pressure liquid chromatography method for producing substantially pure mycoticin A and mycoticin B comprising dissolving mycoticin complex in a methanol-water mixture; injecting the solution into a suitable separation column, using a system of methanol and water as the mobile phase at a flow rate of from about 10 to about 20 ml per minute; detecting the absorption of the effluent at about 300 nm and as a fraction having absorption at about 300 nm is detected, recovering said fraction; combining the fractions with identical retention times; concentrating the combined fractions; and recovering the resultant precipitate.

* * * * *

UNITED STATES PATENT AND TRADEMARK OFFICE
CERTIFICATE OF CORRECTION

PATENT NO. : 5,210,226

DATED : May 11, 1993

INVENTOR(S) : Ramesh C. Pandey

It is certified that error appears in the above-identified patent and that said Letters Patent is hereby corrected as shown below:

ON THE COVER SHEET

IN THE ABSTRACT

"dermostatic A and dermostatic B" should be -- dermostatin A and dermostatin B --.

Column 3, line 30, "bY" should be -- by --.

Column 4, line 18, "10" should be -- 1.0 --.

Column 4, line 46, "23 ≥ 24" should be -- 23-24 --.

Column 5, line 43, "C.," should be --C, --.

Column 5, line 46, "135°-139" should be -- 135-139 --.

UNITED STATES PATENT AND TRADEMARK OFFICE
CERTIFICATE OF CORRECTION

PATENT NO. : 5,210,226
DATED : May 11, 1993
INVENTOR(S) : Ramesh C. Pandey

It is certified that error appears in the above-identified patent and that said Letters Patent is hereby corrected as shown below:

Column 5, line 55, before Mycoticin insert
-- Mycoticin B from the --.

Column 5, line 65, "i.e." should be -- 1.0 --.

Column 6, line 27, "mow" should be -- now --.

Column 6, line 29, "liguid" should be -- liquid --.

Column 6, line 64, "ISR" should be -- IR --.

Signed and Sealed this

Twenty-ninth Day of March, 1994

Attest:

BRUCE LEHMAN

*Attesting Officer*  *Commissioner of Patents and Trademarks*